(12) United States Patent
Mailland

(10) Patent No.: US 7,863,326 B2
(45) Date of Patent: Jan. 4, 2011

(54) PHARMACEUTICAL COMPOSITIONS COMPRISING ASCORBIC ACID FOR THE TREATMENT OF FUNGAL SUPERINFECTIONS AND FUNGAL RECURRENCES

(75) Inventor: Federico Mailland, Milan (IT)

(73) Assignee: Polichem S.A., Luxembourg (LU)

( * ) Notice: Subject to any disclaimer, the term of this patent is extended or adjusted under 35 U.S.C. 154(b) by 1227 days.

(21) Appl. No.: 10/563,912

(22) PCT Filed: May 21, 2004

(86) PCT No.: PCT/EP2004/005559

§ 371 (c)(1),
(2), (4) Date: May 16, 2006

(87) PCT Pub. No.: WO2005/013971

PCT Pub. Date: Feb. 17, 2005

(65) Prior Publication Data

US 2007/0037880 A1    Feb. 15, 2007

(30) Foreign Application Priority Data

Jul. 22, 2003  (EP) ................................. 03077314

(51) Int. Cl.
  A61K 31/375  (2006.01)
  A61K 31/4178 (2006.01)
  A61K 31/4196 (2006.01)
(52) U.S. Cl. .................. 514/474; 514/383; 514/397
(58) Field of Classification Search ................ 514/474, 514/383, 397
See application file for complete search history.

(56) References Cited

U.S. PATENT DOCUMENTS

| 4,229,430 A | 10/1980 | Fahim et al. | |
|---|---|---|---|
| 5,371,107 A * | 12/1994 | Hotzel et al. | ................. 514/474 |
| 5,631,001 A | 5/1997 | Harich et al. | |
| 6,770,306 B1 * | 8/2004 | Zeng | ........................ 424/717 |

FOREIGN PATENT DOCUMENTS

| DE | 299 00 513 U1 | 10/2000 |
|---|---|---|
| EP | 0 527 241 A1 | 2/1993 |
| EP | 1 153 605 A1 | 11/2001 |

OTHER PUBLICATIONS

Kerr. Bacterial inhbition of fungal growth and pathogenicity. Microbial Ecology in Health and Disease pp. 129-142. Scandianavian Univerty Press 1999, ISSN 0891-060X.*
Patent Abstracts of Japan, vol. 2000, No. 09; "Dermatosis Therapeutic Agent and Health Food for Carnivorous Animal", Oct. 13, 2000 & JP 2000 169370 A, Jun. 20, 2000 (abstract).
Patent Abstracts of Japan, vol. 013, No. 372; "Controlling Agent Against Red Rot Fungi"; Aug. 17, 1989 & JP 01 125306 A, May 17, 1989 (abstract).
Database WPI, Derwent Publications Ltd., London, GB; AN 2000-663199.(XP002266917) & RU 2 150 935 C (Univ Mosc Med Stomatology) Jun. 20, 2000 (abstract).
Database WPI, Derwent Publications Ltd., London, GB; AN 2003-002680 (XP002266918); "Antifungal medicinal preparation contains copper (I) oxide, elemental copper and optionally trace elements and ascorbic acid"; & HU 200 004 976 A; Oct. 28, 2002 (abstract).
Fortis, A.A., et al; "Adherence of *Staphylococcus aureus, Klebsiella pneumoniae* and *Candida albicans* to human buccal epithelial cells, from healthy persons and HIV carriers, under the influence of Broncho Vaxom in vitro and ascorbic acid in vivo"; *ACTA Pathologica, Microbiologica, et Immunologica Scandinavica*; vol. 106, No. 4, pp. 441-448 (Apr. 1998) XP009023968 (abstract).
IPER—Vagi-C leaflet; Taurus Pharma, Stand der information, Dec. 2000 (2 pgs).
IPER—Eiko E. Petersen; "Der Einsatz von Vitamin C (Vagi-C) zur Normalisierung der Vaginalflora"; Sounderdruck Gyne; 19, Jahrgang, Mar. 1998.
English translation of German Utility Model DE: 299 00 513 U1; RST Icking GmbH; "Hygiene Agent for Shoes or Feet" (5 pgs).
English translation of Eiko E. Petersen; "Aminocolpitis / Bacterial Vaginosis; Administration of Vitamin C (Vagi-C) for the Normalization of the Vaginal Flora"; *A Journal for Practical Gynecology & General Medicine*, vol. 19, Mar. 1998 (7 pgs).
English translation of Vagi-C leaflet; "Vagi-C®, Vaginal Tablets 250 mg (Ascorbic acid)" (9 pgs).
Runeman, B., et al; "The Vulva Skin Microclimate: Influence of Panty Liners on Temperature, Humidity and pH"; *Acta Derm Venereol*; vol. 83; pp. 88-92 (2003).
Runeman, B., et al; "Experimental *Candida albicans* Lesions in Healthy Humans: Dependence on Skin pH"; *Acta Derm Venereol*; vol. 80; pp. 421-424 (2000).

(Continued)

*Primary Examiner*—Jennifer M Kim
(74) *Attorney, Agent, or Firm*—Nixon & Vanderhye

(57) ABSTRACT

Method for prevention and treatment of vaginal fungal infections by administering a formulation comprising ascorbic acid or a physiologically acceptable salt thereof to a patient in need of such prevention or treatment. The formulation is administered after completion of the standard treatment against bacterial, fungal or protozoarian infections.

16 Claims, No Drawings

OTHER PUBLICATIONS

Runeman, B., et al; "the Vulvar Skin Microenvironment: Influence of Different Panty Liners on Temperature, pH and Microflora"; *Acta Derm Venereol*; vol. 84; pp. 277-284 (2004).

Rogers, T.J., et al; "Dietary ascorbic acid and resistance to experimental renal candidiasis"; *J. Nutr.*; 113(1); pp. 178-183 (1983) (Abstract).

Martindale The complete drug reference; Thirty-third edition, Edited by Sean C. Sweetman; (3 pgs) (2002).

Sobel, J.D., "Vulvovaginal candidosis"; www.thelancet.com; vol. 369; pp. 1961-1971 (2007).

"Cyclopyroxolamine in the Treatment and Prevention of Vulvovaginal Mycoses"; Edited by A.R. Genazzani, et al; The Parthenon Publishing Group; Gorlero, F., et al; "Role of cyclopyroxolamine in mycotic vulvovaginitis: epidemiological prospective study"; pp. 53-64.

Education & Debate; Management of genital candidiasis; *BMJ*; vol. 310, pp. 1241-1244 (1995).

* cited by examiner

PHARMACEUTICAL COMPOSITIONS COMPRISING ASCORBIC ACID FOR THE TREATMENT OF FUNGAL SUPERINFECTIONS AND FUNGAL RECURRENCES

This application is the U.S. National Phase of International Application PCT/EP2004/005559, filed 21 May 2004, which designated the U.S. PCT/EP2004/005559 priority to European Application No. 03077314.7 filed 22 Jul. 2003. The entire content of these applications are incorporated herein by reference.

The present invention relates to compositions containing ascorbic acid or a physiologically acceptable salt thereof as the only active ingredient for the preparation of a medicament, or a medical device, or a sanitary product, useful for the prevention of fungal infection recurrences or fungal superinfections in patients at risk.

Candidiasis, also called thrush, is a fungal, or yeast, infection caused by *Candida albicans*. Although *Candida* is frequently present in the mouth and along the gastrointestinal tract, it does not usually cause illness in people with healthy immune systems. In people with an impaired immune system, however, it often overgrows, producing a characteristic thick, whitish coating.

While candidiasis usually remains confined to the mouth, it can spread to the esophagus and other parts of the gastrointestinal tract and to the respiratory system, posing more serious problems. Esophageal candidiasis, for example, can be extraordinarily uncomfortable, making swallowing difficult and eating painful or, in some cases, impossible.

Other common localization of mycotic infections occur in the genital tract, both of males and females, with vulvovaginal or penile candidiasis. Common mycotic infections of the skin include dermatophytoses, mostly on scalp, on hairy skin and intertriginous areas.

Recurrent vulvovaginal candidiasis (VVC) may be defined as at least four mycologically proven symptomatic episodes in the previous 12 months with exclusion of other common vaginal pathogens. Recurrent VVC does not appear to be the result of resistant vaginal yeast. Male partner should be examined for the presence of penile colonization of *candida* although it has not been confirmed that treatment of men prevents recurrence in women.

Whichever the localization of the pathogen, recurrent candidiasis is a difficult problem to manage. Patients often suffer from depression. They may already have or will develop psychic problems as a result of their illness. Correct diagnosis is vital, and patients should be encouraged to avoid potential precipitating factors, though these may not be obvious. Physical examination, investigations to exclude diabetes mellitus (and possibly HIV infection), and mycological investigation are essential and, if possible, should be performed when the patient has symptoms but has had no treatment (see Denning D. W., BMJ 1995;310:1241-1244).

In the past, clinicians often attributed recurrent vaginal candidiasis to repeated reinoculation of the genital tract from a persistent intestinal reservoir. This belief was based on the finding that patients often harbour the same strain of *C. albicans* in the genital and intestinal tracts. On the other hand, the reduction of intestinal colonisation with *C. albicans*, made by administration of oral nystatin, failed to prevent recurrence of symptoms of vaginal infection.

Asymptomatic colonisation of the male genital tract by *C. albicans* is about four times more common in partners of infected women. The role of sexual transmission in vaginal infection is unknown, and topical or oral treatment of the male partner does not seem to prevent recurrence in the woman. Whatever the source of vaginal reinfection or relapse, women with recurrent candidiasis differ from women with infrequent episodes in being unable to tolerate small numbers of organisms reintroduced or persisting in the genital tract.

Most patients with recurrent candidiasis can be managed with intermittent prophylactic treatment with a single dose or multiple doses of topical or oral antifungals given to prevent symptomatic episodes.

Patients with recurrent candidiasis often resort to home remedies, such as vaginal yoghurt douches or special diets, and some women derive some benefit from them. Other general measures recommended for the prevention of candidiasis include wearing loose fitting cotton underwear and avoiding the wearing of tights altogether. Little data are available on the efficacy of these measures. Likewise, discontinuation of the oral contraceptive pill has little scientific support.

In prospective, controlled studies, women with recurrent vulvovaginal candidiasis had a beneficial effect while on prophylaxis with long-term oral imidazole derivatives, but that relapse was common after withdrawal of the drug. Because of the risk of hepatotoxicity, caution is essential in selecting patients for long-term therapy and in following patients undergoing such treatment, in order to avoid hazard.

Ascorbic acid is very well known in the art (see Martindale, The complete drug reference, 33rd edition, S. C. Sweetman Ed., Pharmaceutical Press 2002). Ascorbic acid (Vitamin C), a water soluble vitamin, is essential for the synthesis of collagen and intercellular material. Vitamin C deficiency develops when the dietary intake is inadequate. It is rare in adults, but may occur in infants, alcoholics, or the elderly. Deficiency leads to the very well defined syndrome known as scurvy. This is, characterized by capillary fragility, bleeding (especially from small blood vessels and the gums) normocytic or macrocytic anaemia, cartilage and bone lesions, and slow healing of wounds. Ascorbic acid is used in the treatment and prevention of deficiency. It completely reverses the symptoms of deficiency. It is usually given by mouth, the preferred route, in form of tablets or capsules, and has been given to children in the form of a suitable fruit juice, such as orange juice or as black currant or rose hip syrups. Water soluble salts of ascorbic acid may be administered parenterally or subcutaneously.

Therapeutically, vitamin C is also used following surgical interventions, as an adjuvant to chelating agent, to increase iron excretion, or in combination to iron compositions, to improve oral absorption of iron, for the faster healing of bone fractures, and as a general tonic. Higher vitamin C doses are recommended as a preventative against catching colds and for speeding up the wound healing. Ascorbic acid is used as an antioxidant in pharmaceutical manufacturing and in the food industry.

A beneficial effect of a "megadose" ascorbic acid therapy has been claimed for an extraordinary number of conditions including asthma, atherosclerosis, cancer, psychiatric disorders, infertility and osteogenesis imperfecta, but there is little evidence of real effectiveness.

A beneficial effect of vaginally applied ascorbic acid has been claimed (see U.S. Pat. No. 5,371,107) in the treatment or prevention of certain bacterial infections, where the pH lowering effect of ascorbic acid plays a role in inhibiting the bacterial growth of strains like Gardnerella or *E. coli* (see Petersen E., Gyne 3, 1998), responsible of infections like bacterial vaginosis. Similarly, a beneficial effect of vaginally applied ascorbic acid has been claimed in the treatment of certain vaginitis of viral origin, though the mechanism of that effect has not been clearly understood. On the other hand, the vaginal application of ascorbic acid has been contraindicated in vaginal mycotic infections, because it is considered useless or potentially dangerous, as fungi in general and *Candida* spp. in particular, unlike bacteria, may easily grow in an acid environment (see Vagi C, Taurus Pharma GmbH, Germany, Gebrauchs information). Furthermore, even when orally supplemented to the diet, any effect of ascorbic acid on the resistance to experimental renal candidiasis in rats was inconclusive, being evident at very low dose but disappearing at a higher dose level (see Rogers T J, J Nutr. 1983;113(1):178-83).

Surprisingly, locally applied ascorbic acid, while being not active or worsening the time course of acute vaginal candidiasis or other fungal infections, was very active in preventing fungal reinfection or superinfection when applied after the completion of a successful standard antimycotic or antibiotic treatment to patients.

This phenomenon leads to the finding that ascorbic acid, being devoid of direct effects on the fungal cells in their vegetative form, creates an unsuitable environment for the germination of new vegetative forms from fungal spores, that was never taught nor suggested by the prior art.

In patients given a standard therapy with metronidazole (for vaginal trichomoniasis or bacteriosis) or miconazole (for vaginal candidiasis), ascorbic acid given after the germ eradication was able to prevent fungal reinfection or superinfection in patients at risk.

DESCRIPTION OF THE INVENTION

The object of the present invention is represented by the use of ascorbic acid or of a physiologically acceptable salt thereof for the preparation of a formulation for the prevention and treatment of fungal infections.

More particularly, it is represented by the use of ascorbic acid or of a physiologically acceptable salt thereof for the preparation of a formulation for the prevention and treatment of fungal infection recurrences (i.e. a second infection caused by the same pathogenic agent) or superinfections (i.e. a second infection caused by a different pathogenic agent).

Semi-solid or liquid preparations of ascorbic acid, in the form of cream, ointment, gel, lotion, foam or collutorium, with a content in ascorbic acid from 0.1 to 25 wt. %, more preferably from 0.5 to 15 wt. %, most preferably from 1.0 to 10%, are suitable to prevent fungal reinfection or superinfection of the scalp, of the skin or of the vagina when applied after a standard antimycotic or antibiotic treatment to patients. Solid preparations, in form of pessaries, tablets or suppositories, with a content in ascorbic acid from 10 to 1000 mg per unit dose, more preferably from 50 to 500 mg per unit dose, most preferably from 100 to 400 mg per unit dose, are suitable to prevent fungal vaginal reinfection or superinfection when applied after a standard antimycotic or antibiotic treatment to patients at risk.

Pharmaceutical compositions, will be prepared according to conventional techniques, using compatible excipients and pharmaceutically acceptable carriers, and may contain, in combination, other active principles with complementary or, in any case, useful activity. Examples of these compositions prepared according to the present invention include: cream, ointment, gel, lotion or foam for either skin (including, but not limited to, external genitals, scalp, intertriginous areas) or vaginal application; moreover tablets, pessaries, capsules for vaginal application; possible forms for delayed melting, intended to prolonged release of the active principle; collutorium for mouthwashes, etc.

The pharmaceutical compositions and the uses of the present invention will now be more fully described by the following examples. It should, however, be noted that such examples are given by way of illustration and not of limitation.

EXAMPLE 1

A gel formulation having the following composition wt./wt. % is prepared:

| | | |
|---|---|---|
| 1. | L-ascorbic acid | 7.1% |
| 2. | glycerin | 5.0% |
| 3. | hydrogenated lecithin | 1.0% |
| 4. | cholesterol | 0.26% |
| 5. | Xanthan Gum | 1.0% |
| 6. | hydroxyethylcellulose | 0.7% |
| 7. | Sodium Methylparaben | 0.37% |
| 8. | Sodium Propylparaben | 0.04% |
| 9. | Imidazolidinyl urea | 0.21% |
| 10. | Disodium EDTA | 0.1% |
| 11. | purified water | 84.22% |

Lecithin and cholesterol were dissolved at 45-50° C. into a minimum amount of ethyl alcohol. This solution was dispersed under stirring into an aqueous solution containing ascorbic acid, glycerin, disodium EDTA, sodium parabenates. After evaporating off the solvent, the remaining ingredients were added under stirring.

The obtained gel had a white, transparent, homogeneous appearance even after prolonged storage. When applied to the skin, or inserted into the vagina by means of an applicator, the gel was able to release ascorbic acid for hours, thus creating a diffuse ascorbic acid film on the entire applied surface.

EXAMPLE 2

A vaginal tablet formulation having the following composition by weight is prepared:

| | | |
|---|---|---|
| 1. | L-ascorbic acid | 250 mg |
| 2. | silicon resin | 10 mg |
| 3. | lactose monohydrate | 690 mg |
| 4. | hydroxypropylmethyl cellulose 2910 | 40 mg |
| 5. | magnesium stearate | 10 mg |

The formulation was prepared by preliminary granulation of the active ingredient, mixing and pressing by standard techniques. First, silicon-coated ascorbic acid and lactose were mixed for 10 minutes in a mixer, wetted with a solution of hydroxypropylmethyl cellulose 2910 in water and granulated for 10 minutes. After drying for 12 hours, the granulate was finely sieved. During sieving, lactose and magnesium were added and the mixture was mixed for 10 minutes in a stainless steel drum, in tumbler motion. The mixture was pressed. The obtained tablets had a white and homogeneous appearance even after prolonged storage. When inserted into the vagina, the tablets were able to release ascorbic acid for hours, thus creating a diffuse ascorbic acid film on the entire vaginal mucosa.

EXAMPLE 3

A collutorium for mouthwashes formulation having the following composition by weight of unit dose is prepared:

| | |
|---|---|
| 1. L-ascorbic acid | 250 mg |
| 2. Sodium carboxymethylcellulose | 150 mg |
| 3. Sodium saccharin | 10 mg |
| 4. Raspberry flavour | 150 mg |
| 5. Sucrose | 4,500 mg |

A water solution of sodium saccharin and sucrose was prepared in a stainless steel dissolver under stirring at 70° C. Sucrose and ascorbic acid were then loaded into a rotogranulator vacuum granulator-desiccator and granulated by spraying the previously prepared solution. The product has been dried under vacuum. Finally, the granulate was transferred to a stainless steel V shaped mixer and sodium carboxymethylcellulose and flavour were added by mixing.

The obtained powder had a white and homogeneous appearance even after prolonged storage. The powder was partitioned in heat-sealed paper-aluminum-polyethylene sachets.

After addition of 50 ml water, the powder formed an extemporary solution. When the solution was used for mouthwashes, it was able to create a diffuse ascorbic acid film on the buccal mucosa.

EXAMPLE 4

Forty women with an exacerbation of recurrent vaginal candidiasis underwent a follow up preventative therapy with ascorbic acid. Most important inclusion criteria were: adult women in fertile age (18-50); ≧3 episodes of acute vaginal candidiasis in the last 12 months; acute vaginal candidiasis in the last 14 days; eradication of *Candida* (fresh examination) after an appropriate miconazole treatment. Exclusion criteria were: severe vaginal infections; HIV positivity; diabetes; pregnant women. The design was double blind, parallel groups versus placebo.

After completion of the standard treatment with miconazole, all the responders (patients with eradication of *Candida* at the end of treatment) were randomized to a standardized preventative vaginal application of ascorbic acid (in form of gel, containing 7.1% ascorbic acid as the only active ingredient, same composition as per the Example 1) or to an undistinguishable placebo. The product was applied once daily in the evening, before going to bed, for 6 consecutive days. The 6-day cycle was repeated monthly for 6 consecutive months, starting on the first month immediately after patient randomization; during the following 5 months, the therapeutic cycle with ascorbic acid was started on the day after termination of cyclic menses. Primary endpoint of the study was the occurrence of episodes of *Candida* reinfection, confirmed by fresh examination of the vaginal smear. In case of reinfection, this was treated with a further standard miconazole treatment and the follow up with ascorbic acid was continued immediately after confirmation of microbiological eradication. All patients in the ascorbic acid group terminated the study, 2 patients of placebo group were lost to follow up. Results showed 15 episodes of reinfection in ascorbic acid group (acute infection:patient rate=0.75/6 months) compared to 25 episodes in placebo group (acute infection:patient rate=1.38/6 months). The protection factor of ascorbic acid against *Candida* reinfection was 46% in this investigation.

EXAMPLE 5

Two hundred patients with a negative microbiology of their vaginal specimen after a standard metronidazole treatment have been included in a controlled study aimed at the evaluation of ascorbic acid capability to prevent *Candida* superinfection in those patients.

The study was randomized, double blind, parallel groups versus placebo. As active treatment, a 6-day course of vaginal tablets, containing 250 mg silicon-coated ascorbic acid as per the Example 2, was given once monthly for 3 months starting after menses. Placebo was undistinguishable from active treatment.

Ninety-five patients in the active group and 92 respectively in the placebo group terminated the study and were included in the efficacy analysis. Results showed a *Candida* superinfection in 14 patients (15%) of placebo group and respectively in 9 patients (9%) of active group. The protection factor of ascorbic acid against *Candida* superinfection in this experiment was 40%.

The invention claimed is:

1. A method for the treatment of a vaginal fungal infection which comprises administering a topical formulation comprising an effective amount of ascorbic acid to a patient in need of such a treatment wherein said formulation is vaginally administered after completion of a standard treatment against bacterial, fungal or protozoarian infections.

2. The method according to claim 1, wherein said formulation is administered after completion of a standard treatment with one or more antimicrobial agents.

3. The method according to claim 2, wherein said antimicrobial agents are selected from the group consisting of antibacteric/antibiotics, antitrichomonas, and antifungal agents.

4. The method according to claim 2, wherein said antimicrobial agents are selected from the group consisting of miconazole and metronidazole.

5. The method according to claim 1, wherein said formulation has an ascorbic acid content of from 0.1 to 25%, with respect to the total weight of the formulation.

6. The method according to claim 5, wherein said formulation has an ascorbic content of from 0.5 to 15% with respect to the total weight of the formulation.

7. The method according to claim 1, wherein said fungal infection is a recurrence.

8. The method according to claim 1, wherein said fungal infection is a superinfection.

9. The method according to claim 1, wherein said fungal infection is caused by *Candida albicans*.

10. The method according to claim 1, wherein said fungal infection is caused by Dermatophytes.

11. The method according to claim 1, wherein ascorbic acid is the only active ingredient contained in the formulation.

12. The method according to claim 1, wherein said formulation comprises additives selected from the group consisting of excipients and adjuvants.

13. The method according to claim 1, wherein ascorbic acid is contained in the formulation in unitary dosages suitable for its application from 10 to 500 mg/day.

14. The method according to claim 1, wherein said formulation is in a form suitable for application to external genitals, intertriginous areas, or for insertion into the vagina.

15. The method according to claim 1, wherein said formulation is in the form of a cream, ointment, gel, lotion, or foam for vaginal application, tablets, pessaries, capsules for vaginal application, a form for delayed melting or a form for prolonged release of said ascorbic acid.

16. Method according to claim 6, wherein said formulation has an ascorbic acid content of from 1.0 to 10% with respect to the total weight of the formulation.

* * * * *